Figure 1:
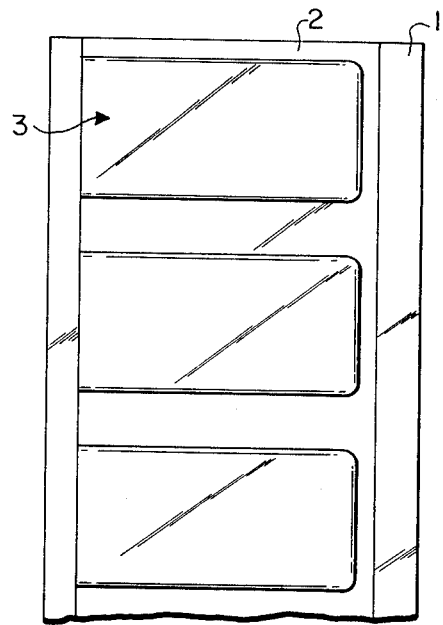

United States Patent [19]

Shave

[11] 4,261,463
[45] Apr. 14, 1981

[54] SUTURE PACKAGE

[75] Inventor: William Shave, Amityville, N.Y.

[73] Assignee: Howmedica Inc., New York, N.Y.

[21] Appl. No.: 821,964

[22] Filed: Aug. 4, 1977

[51] Int. Cl.³ .............................................. A61L 17/02
[52] U.S. Cl. .................................................. 206/63.3
[58] Field of Search .................... 128/1 R, 335, 335.5, 128/339, DIG. 5; 150/1, 14; 206/63.3, 370, 372–373, 379, 472–473, 476, 526-14 527; 229/56

[56] References Cited

U.S. PATENT DOCUMENTS

| | | | |
|---|---|---|---|
| 1,747,010 | 2/1930 | Keller, Jr. | 150/14 X |
| 3,057,471 | 10/1962 | Stonehill et al. | 206/63.3 |
| 3,363,751 | 1/1968 | Shave et al. | 206/63.3 |
| 3,749,233 | 7/1973 | McCormick, Jr. | 206/373 |
| 3,861,521 | 1/1975 | Burtz | 206/63.3 |
| 3,967,666 | 7/1976 | Farrar | 150/1 |
| 4,034,850 | 7/1977 | Mandel et al. | 260/63.3 |

*Primary Examiner*—Herbert F. Ross
*Attorney, Agent, or Firm*—Larson, Taylor and Hinds

[57] ABSTRACT

A suture package is provided comprising an outer sealed package and an inner sterile suture containing package. The inner suture containing package comprises pairs of heat sealed plastic sheets which form a series of pockets which are open at one end. Each of these pockets is adapted to contain a pre-reeled suture disposed within an envelope. Two rows of pockets are sealed together so as to be offset both laterally and vertically to provide a pair of rows of suture containing pockets which are offset with respect to each other for easy access. A portion of the suture within each envelope extends outwardly of the end of the envelope so that the suture may be grasped and withdrawn from the envelope.

2 Claims, 5 Drawing Figures

SUTURE PACKAGE

FIELD OF THE INVENTION

This invention relates to a suture package and more particularly to a suture package comprising an outer sealed package containing a number of individual sutures carried in rows of suture containing pockets. A pair of rows of suture containing pockets is provided within each outer package and each row of sutures is offset laterally and vertically with respect to the other row so as to facilitate access to the individual sutures.

BACKGROUND OF THE INVENTION

It has been well known in the art to provide individual sutures in inner sterile packages which are sealed within an outer package. Packages of this type are shown, for example, in prior U.S. Pat. Nos. 3,147,861 and 3,256,981. The outer package is opened outside the sterile area and the sterile inner package is passed into the sterile operating room. The inner package is opened within the sterile area and the suture within the package can then be used.

There has been a need for providing ready access to the suture once the sterile inner package has been opened. To this end packages such as shown in U.S. Pat. No. 3,363,751 have been developed so that by grasping the needle or a portion of the suture the entire suture can be readily withdrawn from the package. However, there remains the problem of opening a separate outer package to obtain a sterile suture and to do this requires considerable time and effort particularly when a large number of sutures are required within a relatively short space of time.

SUMMARY OF THE INVENTION

This invention provides a means whereby a multiplicity of suture packages can be disposed within a single outer package and these sutures so arranged as to be readily accessible on an individual basis.

According to the present invention there are provided a plurality of individual suture containing pockets which are arranged in a row, with two rows of these suture containing pockets being disposed in offset relation and adapted to be folded within a single outer suture package. Thus, when the outer package is opened and the inner package passed into the sterile area the surgeon has available a multiplicity of individual suture packages. Each of the pockets within the inner package contains an envelope with a portion of a suture extending from the envelope. Thus, the suture can be readily removed by grasping that portion of the suture which extends from the package and withdrawing the entire suture from the envelope and associated pocket. Each suture pocket is offset both vertically and laterally with respect to the next adjacent pocket in the adjacent row. Thus, the sutures can be readily removed from each row without disturbing the remaining sutures.

An object of the present invention is to provide a suture package containing a plurality of sutures which are individually readily accessible.

Another object of the present invention is to provide a suture package comprising an outer sealed package and an inner sterile package including a plurality of open ended pockets disposed in rows, each pocket being adapted to receive an idividual suture so that upon opening the outer package a plurality of individual sutures are made readily accessible.

Figure 2:
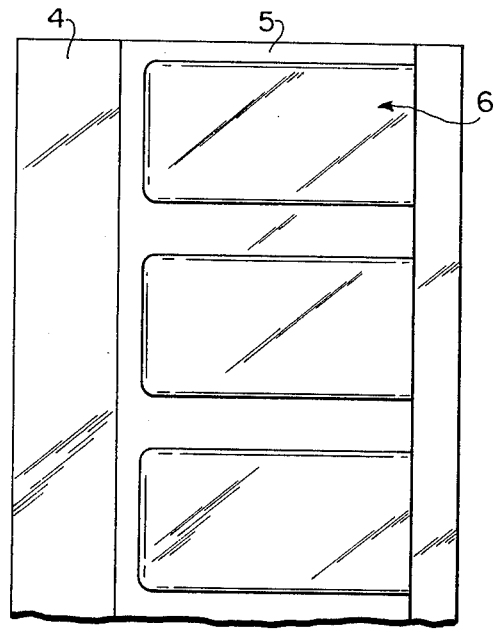
Figure 3:
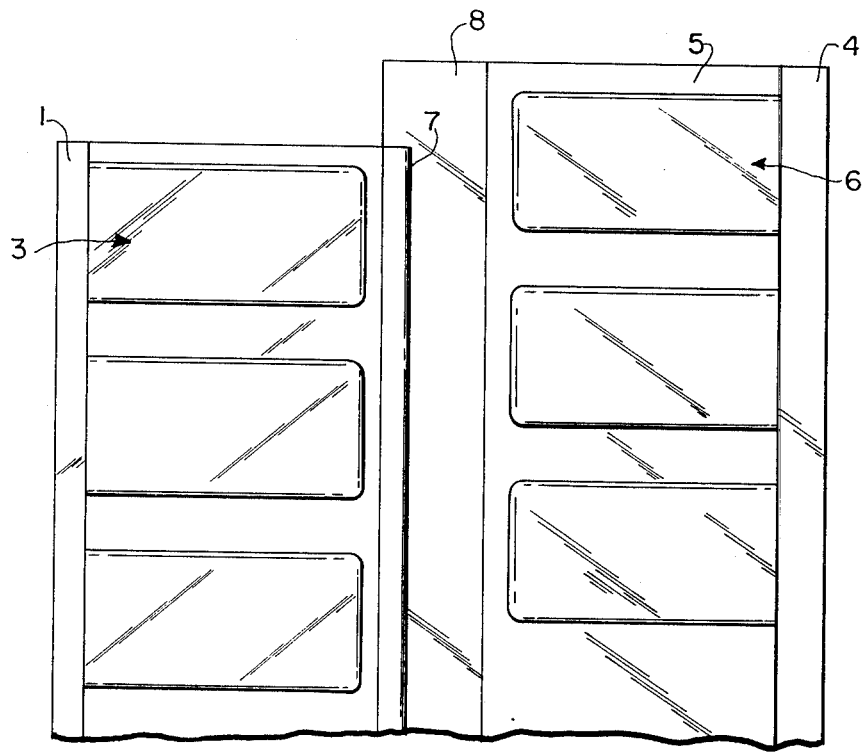
Figure 4:
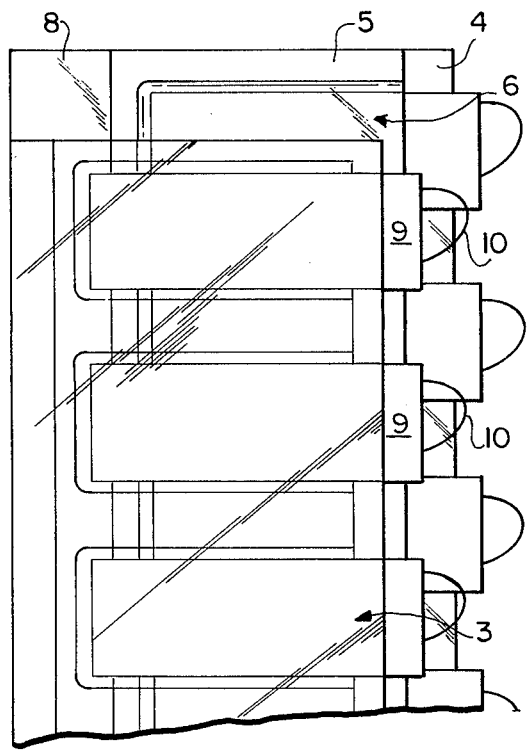
Figure 5:
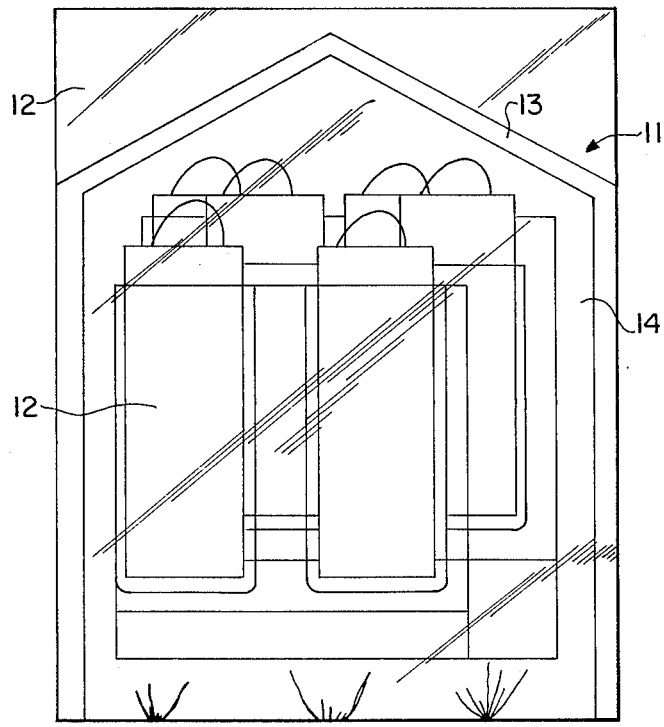

Other objects and many of the attendant advantages of the present invention will become more apparent upon consideration of the following detailed specification in connection with the accompanying drawings wherein:

FIG. 1 is a plan view of a row of suture pockets forming one row of the inner package, FIG. 2 is a plan view of the other row of suture pockets forming the inner package, FIG. 3 is a plan view showing the two rows of suture pockets forming the inner package secured together, FIG. 4 is a plan view of the inner package with each suture pocket containing a suture envelope and suture, and FIG. 5 is a plan view showing the suture inner package within an outer sealed package.

Referring now more particularly to the drawings wherein like numerals indicate like parts throughout the several views there is shown in FIG. 1 a row of suture pockets which are formed with heat sealable film such as polyethylene, a web 1 being heat sealed to a web 2 so as to form a plurality of individual suture pockets shown generally at 3. The web 1 may be slightly larger than the web 2 in width, for example, the web 1 may be 2.5 inches in width whereas the web 2 may be 2 inches in width.

A second row of suture pockets is formed by two further heat sealable plastic films such as is shown at 4 and 5 in FIG. 2. The web 4 is larger than the web 1 in FIG. 1 and may, for example, be 3 inches in width whereas the web 5 may be, for example, 2 inches in width. The webs 4 and 5 are heat sealed together to form individual suture pockets such as shown at 6. Each of the suture pockets 3 in FIG. 1 and 6 in FIG. 2 are heat sealed around three sides to provide an open end along the peripheral edge of the film.

The rows of suture containing pockets as shown in FIGS. 1 and 2 are sealed together along a seal line 7 such as shown in FIG. 3. It can be seen that the row of suture containing pockets shown in FIG. 2 has a relatively wide margin or border area as shown at 8 in FIG. 2 and it is within this border or margin 8 that the row of suture pockets shown in FIG. 1 is heat sealed. It can be seen in FIG. 3 that the suture pockets are offset in one row with respect to the suture pockets in the adjacent row.

Each of the open ended suture pockets shown in FIG. 3 are adapted to be filled with an individual suture envelope such as shown at 9 in FIG. 4. In FIG. 4 it can be seen that each of the suture envelopes 9 has a portion of an individual suture 10 extending therefrom. The two rows of suture containing envelopes are shown in FIG. 4 as being in generally parallel relationship and it can be seen that the individual suture envelopes are spaced both laterally and vertically with respect to each other so that individual sutures 10 are accessible without disturbing the sutures in the remaining suture pockets. As shown in FIG. 4 the suture envelopes 9 project somewhat from the suture pockets so that either the suture envelope can be grasped by the hand to be withdrawn from the suture pocket or, alternatively, the individual suture 10 which projects from the suture envelope can be quickly grasped to withdraw the suture from both the envelope and the pocket.

In FIG. 5 there is shown the inner suture package folded and received within an outer package 11. This outer package may be a so called stripable package such as shown in prior U.S. Pat. No. 3,256,981. It comprises a layer 12 of a thin layer of Mylar or cellophane covering an underlying aluminum foil. The other sheet 14 may be composed of Aclar which is bonded to the polyethylene sheet 11 along a seal line 13. The outer package is not sterile and when the sutures are to be used the outer package is opened and the inner sterile suture package is passed into the sterile area. In use, after the inner package is passed into the sterile area the package may be unfolded so that the sutures are presented to the surgeon for use in the form shown in FIG. 4. The surgeon can grasp the individual suture 10 and quickly withdraw the entire suture and needle combination from the package or, alternatively, the suture envelope can be withdrawn from its associated pocket and opened for use. A multiplicity of individual sutures elements are immediately avaiable for use by opening a single outer suture package.

Obviously many modifications and variations of the present invention are possible in light of the above teachings.

What is claimed is new and desired to be secured by Letters Patent is:

1. A suture package comprising, in combination, a sealed outer strippable package including a pair of heat sealable sheets sealed together to form a sealed outer envelope, a sterile inner suture containing package folded within said sealed outer envelope, said sterile suture containing package comprising two pairs of heat sealable sheets of plastic film, each pair of sheets being sealed together to form a series of open ended pockets, one pair of sheets being secured to the other pair of sheets so that the pockets in one pair of sheets are offset both laterally and longitudinally with respect to the pockets in the other pair of sheets, each pocket containing a suture with a portion of the suture extending from the open end of the pocket whereby the outer strippable package may be opened outside the sterile area and the inner sterile suture containing package passed into the sterile area so that the inner sterile suture containing package may be unfolded to present staggered rows of unpackaged sutures available for immediate use.

2. A suture package according to claim 1 wherein each suture is disposed within an individual envelope within each pocket with a portion of the suture extending from one end of the envelope whereby the suture may be readily grasped and withdrawn from the envelope.

* * * * *